(12) United States Patent
Tang et al.

(10) Patent No.: US 10,674,903 B2
(45) Date of Patent: Jun. 9, 2020

(54) METHOD FOR EVALUATING THE VISION OF AN INDIVIDUAL IN PREDEFINED BRIGHTNESS CONDITIONS

(71) Applicant: ESSILOR INTERNATIONAL, Charenton-le-Pont (FR)

(72) Inventors: David Tang, Charenton-le-Pont (FR); Andrea Molinaro, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 85 days.

(21) Appl. No.: 15/775,969

(22) PCT Filed: Nov. 17, 2016

(86) PCT No.: PCT/FR2016/052991
§ 371 (c)(1),
(2) Date: May 14, 2018

(87) PCT Pub. No.: WO2017/089681
PCT Pub. Date: Jun. 1, 2017

(65) Prior Publication Data
US 2018/0325369 A1    Nov. 15, 2018

(30) Foreign Application Priority Data
Nov. 25, 2015  (FR) ...................................... 15 61368

(51) Int. Cl.
*A61B 3/02* (2006.01)
*A61B 3/032* (2006.01)
*A61B 3/06* (2006.01)

(52) U.S. Cl.
CPC .............. *A61B 3/022* (2013.01); *A61B 3/032* (2013.01); *A61B 3/06* (2013.01)

(58) Field of Classification Search
CPC ........... A61B 3/02; A61B 3/022; A61B 3/024; A61B 3/028; A61B 3/032; A61B 3/06; A61B 3/1015; G09G 3/20; G09G 3/2011
(Continued)

(56) References Cited

U.S. PATENT DOCUMENTS

| | | | |
|---|---|---|---|
| 4,861,156 A | 8/1989 | Terry | |
| 2004/0036840 A1* | 2/2004 | Marino | A61B 3/0033 351/239 |

(Continued)

FOREIGN PATENT DOCUMENTS

| | | |
|---|---|---|
| EP | 1 236 433 A1 | 9/2002 |
| JP | H11 212526 A | 8/1999 |

(Continued)

OTHER PUBLICATIONS

English translation of JP EP 1236433, machine translated on Jul. 31, 2019.*

(Continued)

*Primary Examiner* — Jie Lei
(74) *Attorney, Agent, or Firm* — Young & Thompson

(57) ABSTRACT

Disclosed is a method for evaluating the vision of an individual under certain brightness conditions, using a screen displaying an image including a background and characters to be deciphered which appear on the background. The method includes the following steps: a step of regulating the brightness of the background of the image; and a step of regulating the brightness of the characters to be deciphered which appear on the image, the two steps being independent from each other so as to obtain the desired contrast between the background and the characters.

20 Claims, 1 Drawing Sheet

(58) Field of Classification Search
USPC .......................... 351/239, 237, 222, 243, 246
See application file for complete search history.

(56) References Cited

U.S. PATENT DOCUMENTS

2004/0100616 A1   5/2004   Eremeev
2014/0285769 A1*  9/2014   Palanker ................ G06Q 50/22
                                                 351/223

FOREIGN PATENT DOCUMENTS

WO       02/076301 A1    10/2002
WO    2013/059331 A1     4/2013
WO    2015/028721 A1     3/2015

OTHER PUBLICATIONS

International Search Report, dated Feb. 10, 2017, from corresponding PCT/FR2016/052991 application.
FR Search Report, dated Oct. 4, 2016, from corresponding FR 1561368 application.

* cited by examiner

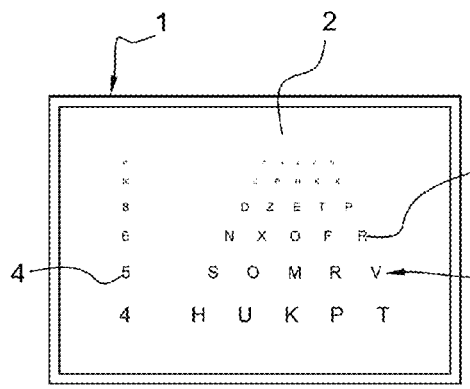 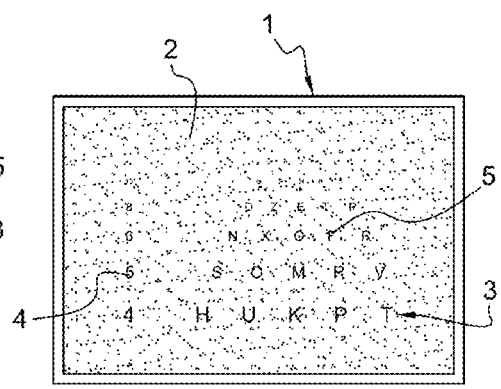
Fig. 1  Fig. 2
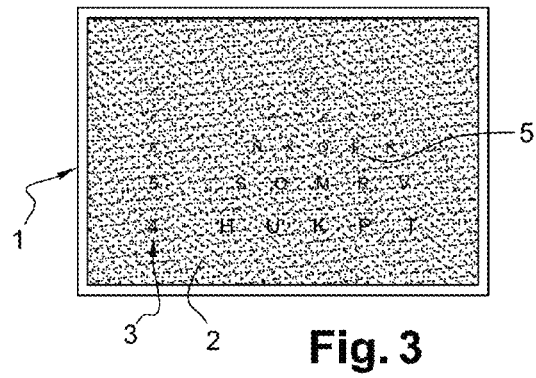
Fig. 3
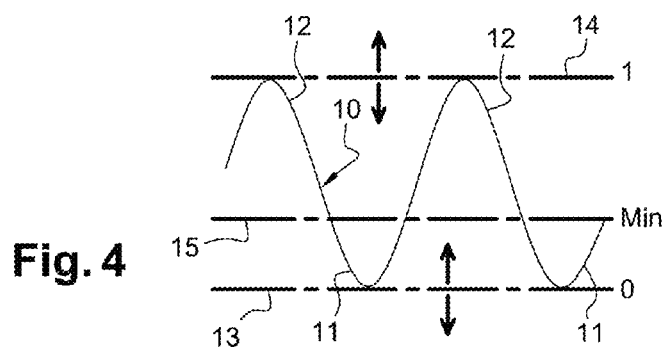
Fig. 4

METHOD FOR EVALUATING THE VISION OF AN INDIVIDUAL IN PREDEFINED BRIGHTNESS CONDITIONS

The invention relates to a method for evaluating the vision of an individual under predefined luminance conditions.

BACKGROUND OF THE INVENTION

Simple tests allowing the quality of the vision of an individual to be evaluated under particular luminance conditions, and in particular when this luminance is low, or even very low, do exist.

It will be recalled that mesopic vision corresponds to vision of a scene the luminance of which is comprised between 3 and 10 cd/m2, and scotopic vision corresponds to vision of a scene the luminance of which is below 0.001 cd/m2.

Existing digital screens are unable to manage a display with such low luminance levels. Specifically, to reconstruct the conditions of a night scene, it is necessary to decrease the brightness of the screen to a lower level than manufacturers currently allow via their pages for parameterizing screen brightness.

Currently, the tests used to examine an individual's perception of contrast are carried out with pieces of apparatus employing characters to be viewed, these characters possibly for example being represented by a text and/or figures printed on transparent films. However, these pieces of apparatus have two limitations:
1—In order to test a maximum number of contrasts with a given plate, only a few characters are displayed with a given contrast level, and the various test configurations usable to test the vision of an individual are greatly limited;
2—To remedy the preceding limitation, it is necessary to multiply the number of test plates in order to allow a multiplicity of configurations usable to evaluate the vision of the individual to be achieved.

Two major drawbacks result from these limitations, namely, on the one hand, the additional costs associated with the multiplication of the test plates and with the manufacture thereof, and, on the other hand, the substantial bulk associated with the multiplication of the test plates. In addition, in a technology involving a drum around which the test plates are placed, there remains less space for other types of tests.

SUMMARY OF THE INVENTION

An evaluating method according to the invention allows the vision of an individual to be evaluated in a multiplicity of configurations each corresponding to a given luminance contrast, while avoiding the drawbacks of the prior art.

One subject of the invention is a method for evaluating the vision of an individual under predefined luminance conditions, using a screen presenting an image comprising a background and characters to be deciphered appearing on said background.

The main feature of an evaluating method according to the invention is that it comprises the following steps,
 a step of adjusting the luminance of the background of the image,
 a step of adjusting the luminance of the characters to be deciphered appearing in the image, said two steps being independent from each other so as to obtain the desired contrast between the background and the characters.

The principle of such a method is to make an individual view the various visible characters appearing on the background of the image, with a desired luminance contrast between said background and said characters. By separately adjusting the luminance of the background of the image and the luminance of the visible characters, it becomes possible to test the vision of the individual in a very large number of configurations, each characterized by a contrast between the luminance of the characters and the luminance of the background. By virtue of a separate adjustment of the luminance of the background and of the luminance of the characters, a method according to the invention is perfectly suitable for evaluating the mesopic vision and the scotopic vision of an individual. Specifically, it is enough to adjust the background of the image to a given grayscale level to obtain the desired background luminance, then to tailor, if necessary, the grayscale level of the characters, in order to obtain the desired contrast between the characters and the background of the image and thus to reproduce an image that is representative of a night scene to be viewed. With a conventional computer, it is impossible to test the scotopic vision of an individual by darkening the background of the image, because it is not possible to separately adjust the luminance of the characters to make the characters readable. In contrast, using a method according to the invention, it is enough to act on the particular luminances of the characters to be deciphered and of the background to make a contrast appear, between the luminance of said characters and the luminance of said background, that is representative of a night configuration. In a method according to the invention, the characters to be deciphered and the background may be grayscale and/or in color. The characters to be deciphered may be of any nature, and may for example correspond to separate letters or letters forming a text, to numbers, to a mixture of numbers and letters, to geometric figures, to separate or mixed color palettes, etc. The term "screen" is generic and covers any device able to make appear an image with a background and characters to be deciphered. Such a device may, for example, be represented by a device with a light bulb, or by a computer screen.

Advantageously, for detection of night vision, the luminance of the characters and the luminance of the background are variable. It is enough therefore to set a luminance for the background, then to tailor the luminance of the characters to be deciphered to said luminance of the background, to reproduce the conditions of a night scene.

Preferably, the image appearing on the screen is characterized by pixels, the luminance of the background of the image and the luminance of the characters being adjusted at the level of said pixels. Each pixel may have a plurality of grayscale levels or a plurality of colors, and therefore allows a multiplicity of different luminances to be obtained. By virtue of these many possible grayscale levels and colors, the luminance of the background and of the characters to be deciphered may be finely and therefore very precisely adjusted.

Preferably, the luminance of the background of the image is adjusted to relatively dark grayscale levels in order to simulate the conditions of night vision. To reproduce the conditions of a night scene, it is important to respect a certain level of luminance contrast between the background and the characters to be deciphered.

Advantageously, the luminance of the background is adjusted to a given grayscale level and the luminance of the characters is adjusted to a grayscale level dependent on the grayscale level of said background, so as to control both the luminance of the background of the image but also the displayed contrast between the background and the characters. In this way, it is not only possible to simulate a night scene by means of an adjustment of the grayscale level of the background of the image, in order to evaluate the mesopic and scotopic vision of the individual, but also to simulate an entire desired panel of contrasts by adjusting the grayscale level of the characters.

Advantageously, the background of the image and the characters are in color. The screen may thus make an image appear the background of which has a variable color and the characters of which also have their own color, which may be different from that of the background or be analogous to that of said background but with a different intensity.

Advantageously, an evaluating method according to the invention comprises a step of evaluating the mesopic vision of an individual. The luminance of the background and of the characters to be deciphered are adjusted so as to reproduce a visible scene in the tailored luminance range. An evaluating method according to the invention is particularly suitable for evaluating the vision of an individual at low luminance levels.

According to another but preferred embodiment of an evaluating method according to the invention, said method comprises a step of evaluating the scotopic vision of an individual. The luminance of the background and of the characters to be deciphered are adjusted so as to reproduce a visible scene in the tailored luminance range. An evaluating method according to the invention is particularly suitable for evaluating the vision of an individual at very low luminance levels, in order to simulate vision of a night scene.

Another subject of the invention is a device for displaying an image in order to allow a method according to the invention to be implemented, said device comprising a screen able to display an image comprising a background and characters appearing on said background.

The main feature of a displaying device according to the invention is that it comprises controlling means that are able to independently control the luminance of the background and the luminance of the characters to be deciphered.

Advantageously, the image is made up of pixels, and said controlling means act on said pixels in order to modify the luminance of the background and of the characters.

Preferably, the controlling means are able to adjust the grayscale level or the color of each pixel.

Preferably, a displaying device according to the invention consists of a tablet, able to be manipulated by an individual desiring to test his vision under certain luminance conditions. The tablet may be a touch tablet, the commands that control the luminance of the background of the image and of the characters to be deciphered being triggered by pressure on the screen in indicated locations.

A method for evaluating the vision of an individual according to the invention has the advantage of testing the vision of an individual via a plurality of scenes having different luminance contrasts, without involving a bulky apparatus that is difficult to manipulate. In addition, it has the advantage of not only being particularly suitable for evaluating the night vision of an individual, but of also being able to implement a multiplicity of tests involving various grayscale levels and/or different colors with predefined luminance contrasts.

BRIEF DESCRIPTION OF THE DRAWINGS

A detailed description of one particular embodiment of an evaluating method according to the invention is given below with reference to the following:

FIG. 1 is an example of a screen capture of a screen allowing the day visual acuity of an individual to be evaluated, FIG. 2 is a first example of a screen capture of a screen allowing the night vision of an individual to be evaluated, FIG. 3 is a second example of a screen capture of a screen allowing the night vision of an individual to be evaluated, FIG. 4 is a graph of the luminance of a screen background and of the luminance of characters to be deciphered along an x-axis of a screen for implementing an evaluating method according to the invention.

DETAILED DESCRIPTION OF THE PREFERRED EMBODIMENTS

A device for displaying an image 1 for implementing a method according to the invention allowing the vision of an individual to be tested under certain luminance conditions comprises a screen able to display an image made up of pixels. It will be recalled that a color, usually decomposed into three primary components, namely red, green and blue, is associated with each pixel. Thus, each pixel is able to generate 255 grayscale levels between white and black, and a multiplicity of colors. Such a displaying device may for example take the form of a computer or a touch tablet.

Generally, a method for evaluating the vision of an individual under certain luminance conditions is carried out by means of the display of a least one image 1 that is representative of a scene to be viewed having a given luminance.

Thus, with reference to FIGS. 1, 2, 3 and 4, each image 1 has a background 2 having a particular color and characters 3 to be deciphered having a different color from that of said background 2. These characters 3 to be deciphered may for example appear in the form of numbers 4, of letters 5 and/or of any particular geometric shapes and/or of colored zones.

FIG. 1 illustrates an example of a conventional image delivered by a screen and allowing the day visual acuity of an individual to be evaluated. To this end, this image 1 possesses a white background 2 and horizontal rows of characters 3 in black, taking the form of a number 4 and a plurality of letters 5. In other words, each row contains characters 3 all having the same size, two separate rows containing characters of different size. Each row contains a number 4 located on the left of the screen and a series of five letters 5 that are regularly spaced and located on the right of said number 4. All the numbers 4 of the various rows are aligned vertically to form a column. An individual placed a few meters from the image and equipped or not with a frame with corrective lenses, attempts to decipher all the characters 4, 5 of a given row. He may thus determine up to what row of characters 4, 5 he is able to read said characters 4, 5 without difficulty i.e. the row of smallest characters that he is able to read without difficulty.

Present-day screens propose only a few possibilities as regards images for testing the visual acuity of an individual, and more particularly the ability of an individual to see contrasts. The background 2 generally remains white, and the characters 3 to be deciphered have a few grayscale levels and/or a few colors, the luminance of said background 2 and said characters 3 remaining uniform. The possibilities as regards images delivered with present-day screens for testing the vision of an individual under various luminance conditions are limited.

To test the night vision of an individual, whether this be his mesopic vision or his scotopic vision, it is proposed, with present-day screens, as indicated in FIG. 3, to manipulate a conventional luminance control of the screen, in order to uniformly darken said screen, i.e. such that both the background 2 of the image and of the characters 3 to be deciphered appearing on said background 2 become darker. However, the luminance of the background 2 of the image 1 cannot be decreased sufficiently to allow mesopic or scotopic conditions to be achieved.

In addition, present-day computer or tablet screens, since they are equipped only with a single luminance control that uniformly adjusts the luminance of the background 2 of the image 1 and the luminance of the characters 3 to be deciphered, therefore do not allow the relative displayed contrast between the characters 3 and the background 2 of the image 1 to be varied, for a given luminance of the background 2.

A method according to the invention for evaluating an individual's visual acuity and/or ability to see contrasts or even colors at night is based on the principle of independent adjustment of the luminance of the background 2 of the image and of the luminance of the characters 3 to be deciphered. In this way, by allowing the luminance of the background 2 of the image 1 and the luminance of the characters 3 to be deciphered to be adjusted separately, a method according to the invention is not only perfectly suitable for rigorous and realistic evaluation of the night vision of an individual, but is also suitable for evaluating this type of vision in a multiplicity of situations involving various grayscale levels and/or various colors. Thus, in order to simulate a night scene with a method according to the invention, the luminance of the background 2 of the image is adjusted in order to bring said background 2 to a certain grayscale level, and the luminance of the characters 3 to be deciphered is adjusted independently of the luminance of said background 2, so that the luminance difference between the background 2 and the characters 3 is representative of that of a night scene.

A method according to the invention thus allows the following functions to be obtained in a digital screen:
  Ability to adjust the luminance of the background 2 of the image 1 beyond what is possible with a present-day digital screen.
    By displaying the scene on a gray background and not on a white background, the illusion is given of having a sufficiently low luminance level to simulate a scene seen with (mesopic or scotopic) night vision;
    More generally allows the luminance of the background 2 of the image 1 to be adjusted beyond what is possible with a present-day digital screen, and may therefore allow luminance cases other than mesopic or scotopic cases to be envisioned.
  Ability to adjust the luminance of the displayed characters 3 continuously via adjustment of their grayscale level or their color, by means of a simple manipulation, in order to obtain the desired contrast with the background 2 of the image 1.

Therefore, a method for evaluating the mesopic or scotopic vision of an individual according to the invention consists in adjusting the luminance of the background 2 of the image 1 in order to obtain a desired grayscale level, then adjusting, if necessary, the luminance of the characters 3 to be deciphered so that the ensemble formed by the background 2 and the characters 3 is representative of a night scene.

The principle of an evaluating method according to the invention is summarized in the graph of FIG. 4.

The curve 10 represents, in terms of luminance, the image to be displayed as a function of distance along the x-axis of the screen. Thus, the low zones 11 of this sinusoidal curve indicate the presence of a character 3 to be deciphered, and the high zones 12 indicate screen spaces located between two successive characters 3. The curve 13 represents the luminance level of the characters 3 to be deciphered of the image 1, which may be adjusted as required. The curve 14 represents the luminance level of the background 2 of the image 1, which may be adjusted as required. The curve 15 represents the minimum luminance level below which the luminance of the background 2 of the image 1 cannot be decreased via the standard display brightness adjustment proposed by screen manufacturers. A method according to the invention allows the curves 13 and 14 to be adjusted independently, this amounting to independent adjustment of the luminance of the background 2 of the image 1 (this adjustment even allowing a decrease to below the minimum value that it is possible to achieve with standard screen brightness adjustments) and of the luminance of the characters 3 to be deciphered.

A method according to the invention, by virtue of the flexibility of adjustment of the background 2 of the image 1 and of the flexibility of adjustment of the characters 3 to be deciphered, may be applied to all currently available tests, such as, for example, tests of visual acuity, tests of stereoscopic vision, fusion tests, color tests, etc.

Present-day digital screens do not allow all these tests to be carried out because it is impossible therewith to not only adjust the luminance of the background 2 of the image 1 to a sufficiently low level, i.e. to below the level represented by the curve 15, but also to disassociate the adjustment of the luminance of the background 2 of the image 1 and the adjustment of the luminance of the characters to be deciphered, this considerably decreasing the number of test configurations.

By separately varying the components of the base colors (red, green, blue) of the pixels composing the image 1, it is possible to tailor this operation to tests for measuring contrasts perceived with various color cones.

In addition, by combining the variation in the luminance of the background 2 of the image with the variation in the luminance of the characters 3, it is thus possible to maintain a desired contrast level and to only make the displayed luminance vary to a desired level.

Lastly, this technique also allows calibration of colorimetry to be carried out with regard to adjustment of color temperatures, but also allows the luminance or the colors of the images to be automatically adjusted if the apparatus is equipped with a suitable sensor.

The invention claimed is:

1. A method for evaluating the vision of an individual under predefined luminance conditions, using a screen presenting an image (1) that includes a background (2) and characters (3) to be deciphered appearing on said background (2), the method comprising:
  a step of adjusting a luminance of the background (2) of the image (1);
  a step of adjusting a luminance of the characters (3) to be deciphered appearing in the image (1),
  said steps of adjusting the luminance of the background and adjusting the luminance of the characters being independent from each other so as to obtain a desired contrast between the background (2) and the characters (3); and
  evaluating the vision of the individual based on the image characterized by the obtained contrast, wherein the method further comprises:
a step of adjusting the background to a given grayscale level to obtain a desired background luminance; and
a step of tailoring a grayscale level of the characters to obtain the desired contrast between the background and the characters, thereby to reproduce the image as representative of a night scene to be viewed by the individual.

2. The evaluating method as claimed in claim 1,
wherein the image (1) appearing on the screen is characterized by pixels, and
wherein the luminance of the background (2) of the image (1) and the luminance of the characters (3) is adjusted at a level of said pixels.

3. The evaluating method as claimed in claim 2, wherein the luminance of the background (2) of the image (1) is adjusted to relatively dark grayscale levels in order to simulate the conditions of night vision.

4. The evaluating method as claimed in claim 3, wherein the luminance of the characters (3) is adjusted to a grayscale level dependent on the grayscale level of said background (2), so as to control both the luminance of the background (2) of the image (1) and the displayed contrast between the background (2) and the characters (3).

5. The evaluating method as claimed in claim 3, wherein the vision evaluated of the individual is a mesopic vision of the individual.

6. The evaluating method as claimed in claim 3, wherein the vision evaluated of the individual is a scotopic vision of the individual.

7. The evaluating method as claimed in claim 2, wherein the luminance of the characters (3) is adjusted to a grayscale level dependent on the grayscale level of said background (2), so as to control both the luminance of the background (2) of the image (1) and the displayed contrast between the background (2) and the characters (3).

8. The evaluating method as claimed in claim 7, wherein the vision evaluated of the individual is a mesopic vision of the individual.

9. The evaluating method as claimed in claim 7, wherein the vision evaluated of the individual is a scotopic vision of the individual.

10. The evaluating method as claimed in claim 2, wherein the background (2) of the image (1) and the characters (3) are in color.

11. The evaluating method as claimed in claim 2, wherein the vision evaluated of the individual is a mesopic vision of the individual.

12. The evaluating method as claimed in claim 2, wherein the vision evaluated of the individual is a scotopic vision of the individual.

13. The evaluating method as claimed in claim 1, wherein the vision evaluated of the individual is a mesopic vision of the individual.

14. The evaluating method as claimed in claim 1, wherein the vision evaluated of the individual is a scotopic vision of the individual.

15. A device for displaying an image for implementing the method claimed in claim 1, said device comprising a screen that displays an image (1) that includes a background (2) and characters (3) appearing on said background (2), and controlling means that independently control the luminance of the background (2) and the luminance of the characters (3) to be deciphered by the individual.

16. The displaying device as claimed in claim 15,
wherein the image (1) is formed of pixels, and
wherein said controlling means operate on said pixels in a manner so as to modify the luminance of the background (2) and of the characters (3).

17. The displaying device as claimed in claim 16, wherein the controlling means adjust the grayscale level or the color of each pixel.

18. The displaying device as claimed in claim 15, wherein said displaying device is a tablet configured to be manipulated by the individual to test the vision of the individual under the predefined luminance conditions.

19. A device that displays an image for evaluating the vision of an individual under predefined luminance conditions, comprising:
a screen that displays an image (1) that includes a background (2) and characters (3) to be deciphered by the individual displayed on said background (2); and
controlling means that independently control the luminance of the background (2) and the luminance of the characters (3),
said controlling means configured for adjusting a luminance of the background (2) of the image (1), and adjusting a luminance of the characters (3) appearing in the image (1), said adjusting the luminance of the background and adjusting the luminance of the characters being independent from each other so as to obtain a desired contrast between the background (2) and the characters (3), and
said controlling means further configured for adjusting the background to a given grayscale level to obtain a desired background luminance, and for adjusting a grayscale level of the characters to obtain the desired contrast between the background and the characters, thereby to reproduce the image as representative of a night scene to be viewed by the individual.

20. The device as claimed in claim 19,
wherein the screen is constituted by pixels, the image (1) being formed by said pixels, and
wherein said controlling means operate on said pixels in a manner so as to modify the luminance of the background (2) and of the characters (3) of the image.

* * * * *